(12) United States Patent
Dutoit et al.

(10) Patent No.: US 8,147,493 B2
(45) Date of Patent: Apr. 3, 2012

(54) BONE-FIXATION DEVICE

(75) Inventors: Christof Dutoit, Solothurn (CH); André Frenk, Solothurn (CH); Philippe Chelius, Clerey (FR)

(73) Assignee: Synthes USA, LLC, West Chester, PA (US)

( * ) Notice: Subject to any disclaimer, the term of this patent is extended or adjusted under 35 U.S.C. 154(b) by 1078 days.

(21) Appl. No.: 11/371,773

(22) Filed: Mar. 8, 2006

(65) Prior Publication Data

US 2006/0217722 A1    Sep. 28, 2006

Related U.S. Application Data

(63) Continuation of application No. PCT/CH03/00604, filed on Sep. 8, 2003.

(51) Int. Cl.
*A61B 17/56*    (2006.01)

(52) U.S. Cl. .......................................... 606/65; 606/284

(58) Field of Classification Search .................... 606/70, 606/71, 913, 62–68, 280–299; 623/20.35, 623/20.36
See application file for complete search history.

(56) References Cited

U.S. PATENT DOCUMENTS

| | | | |
|---|---|---|---|
| 2,406,832 A * | 9/1946 | Hardinge | ........................ 606/71 |
| 2,612,159 A | 9/1952 | Collison | |
| 3,463,148 A | 8/1969 | Treace | |
| 3,552,389 A | 1/1971 | Allgower et al. | |
| 3,630,261 A | 12/1971 | Gley | |
| 3,668,972 A | 6/1972 | Allgower et al. | |
| 3,716,050 A | 2/1973 | Johnston | |
| 3,741,205 A | 6/1973 | Markolf et al. | |
| 3,779,240 A | 12/1973 | Kondo | |
| RE28,841 E | 6/1976 | Allgower et al. | |
| 4,029,091 A | 6/1977 | Von Bezold et al. | |
| 4,095,591 A | 6/1978 | Graham, Jr. et al. | |
| 4,175,555 A | 11/1979 | Herbert | |
| 4,219,015 A | 8/1980 | Steinemann | |
| 4,263,904 A | 4/1981 | Judet | |
| 4,338,926 A | 7/1982 | Kummer et al. | |
| 4,408,601 A | 10/1983 | Wenk | |

(Continued)

FOREIGN PATENT DOCUMENTS

CA    1112803    11/1981

(Continued)

OTHER PUBLICATIONS

Machine translation JP 11-299804. 14 pages.*

(Continued)

*Primary Examiner* — Eduardo C Robert
*Assistant Examiner* — Jerry Cumberledge
(74) *Attorney, Agent, or Firm* — Fay Kaplun & Marcin, LLP

(57) ABSTRACT

The invention relates to a trochanter stabilizing device (40), especially for fixing bone fragments in the region of the hip joint (11) or for fixing the greater trochanter (12), including A) bone stabilizing means (1) consisting of a central plate (2) with at least one fixing perforation (13) for receiving a bone fixing means (20); B) a longitude bone plate (30) with a bushing (31) arranged at an angle for receiving a fixing element (50) which can be introduced into the region of the hip joint (11) fixed thereto, whereby C) at least three peripheral arms (4) originate from the central plate (2), whereby D) each peripheral arm (4) is provided with at least one hole (5) for receiving a bone fixing means (20).

24 Claims, 3 Drawing Sheets

U.S. PATENT DOCUMENTS

| | | | |
|---|---|---|---|
| 4,429,690 A | 2/1984 | Angelino-Pievani | |
| 4,432,358 A | 2/1984 | Fixel | |
| RE31,628 E | 7/1984 | Allgower et al. | |
| 4,484,570 A | 11/1984 | Sutter et al. | |
| 4,493,317 A | 1/1985 | Klaue | |
| 4,513,744 A | 4/1985 | Klaue | |
| 4,530,355 A | 7/1985 | Griggs | |
| 4,565,193 A | 1/1986 | Streli | |
| 4,612,920 A | 9/1986 | Lower | |
| 4,612,923 A | 9/1986 | Kronenthal | |
| 4,651,724 A | 3/1987 | Berentey et al. | |
| 4,657,001 A | 4/1987 | Fixel | |
| 4,683,878 A | 8/1987 | Carter | |
| 4,776,329 A | 10/1988 | Treharne | |
| 4,781,183 A | 11/1988 | Casey et al. | |
| 4,838,252 A | 6/1989 | Klaue | |
| 4,858,601 A | 8/1989 | Glisson | |
| 4,867,144 A | 9/1989 | Karas et al. | |
| 4,927,421 A | 5/1990 | Goble et al. | |
| 4,957,497 A | 9/1990 | Hoogland et al. | |
| 4,973,332 A * | 11/1990 | Kummer | 606/65 |
| 4,988,350 A * | 1/1991 | Herzberg | 606/65 |
| 5,002,544 A | 3/1991 | Klaue et al. | |
| 5,006,120 A | 4/1991 | Carter | |
| 5,007,910 A | 4/1991 | Anapliotis et al. | |
| 5,032,125 A | 7/1991 | Durham et al. | |
| 5,041,113 A | 8/1991 | Biedermann et al. | |
| 5,041,114 A | 8/1991 | Chapman et al. | |
| 5,053,036 A | 10/1991 | Perren et al. | |
| 5,085,660 A | 2/1992 | Lin | |
| 5,127,914 A | 7/1992 | Calderale et al. | |
| 5,129,901 A | 7/1992 | Decoste | |
| 5,129,903 A * | 7/1992 | Luhr et al. | 606/71 |
| 5,151,103 A | 9/1992 | Tepic et al. | |
| 5,190,544 A | 3/1993 | Chapman et al. | |
| 5,197,966 A | 3/1993 | Sommerkamp | |
| 5,269,784 A | 12/1993 | Mast | |
| 5,275,601 A | 1/1994 | Gogolewski et al. | |
| 5,304,180 A | 4/1994 | Slocum | |
| 5,324,290 A | 6/1994 | Zdeblick et al. | |
| 5,336,224 A | 8/1994 | Selman | |
| 5,360,429 A * | 11/1994 | Jeanson et al. | 606/250 |
| 5,360,448 A | 11/1994 | Thramann | |
| 5,364,398 A | 11/1994 | Chapman et al. | |
| 5,364,399 A | 11/1994 | Lowery et al. | |
| 5,429,641 A | 7/1995 | Gotfried | |
| 5,454,813 A | 10/1995 | Lawes | |
| 5,462,547 A | 10/1995 | Weigum | |
| 5,501,684 A | 3/1996 | Schlapfer et al. | |
| 5,514,138 A | 5/1996 | McCarthy | |
| 5,591,168 A | 1/1997 | Judet et al. | |
| 5,601,553 A | 2/1997 | Trebing et al. | |
| 5,607,426 A * | 3/1997 | Ralph et al. | 606/287 |
| 5,607,428 A | 3/1997 | Lin | |
| 5,674,222 A | 10/1997 | Berger et al. | |
| 5,690,631 A * | 11/1997 | Duncan et al. | 606/281 |
| 5,702,399 A | 12/1997 | Kilpela et al. | |
| 5,709,686 A | 1/1998 | Talos et al. | |
| 5,735,853 A | 4/1998 | Olerud | |
| 5,741,258 A | 4/1998 | Klaue et al. | |
| 5,743,913 A * | 4/1998 | Wellisz | 606/285 |
| 5,749,872 A | 5/1998 | Kyle et al. | |
| 5,772,662 A | 6/1998 | Chapman et al. | |
| 5,779,703 A * | 7/1998 | Benoist | 606/54 |
| 5,810,823 A | 9/1998 | Klaue et al. | |
| 5,843,082 A | 12/1998 | Yuan et al. | |
| 5,871,485 A * | 2/1999 | Rao et al. | 606/65 |
| 5,871,548 A * | 2/1999 | Sanders et al. | 623/22.36 |
| 5,908,422 A | 6/1999 | Bresina | |
| 5,938,664 A | 8/1999 | Winquist et al. | |
| 5,954,722 A | 9/1999 | Bono | |
| 5,968,047 A | 10/1999 | Reed | |
| 5,976,141 A | 11/1999 | Haag | |
| 6,004,353 A * | 12/1999 | Masini | 623/22.21 |
| 6,022,352 A | 2/2000 | Vandewalle | |
| 6,093,188 A * | 7/2000 | Murray | 606/282 |
| 6,096,040 A | 8/2000 | Esser | |
| 6,129,728 A * | 10/2000 | Schumacher et al. | 606/71 |
| 6,129,730 A | 10/2000 | Bono et al. | |
| 6,139,552 A | 10/2000 | Horiuchi | |
| 6,183,475 B1 | 2/2001 | Lester et al. | |
| 6,206,881 B1 | 3/2001 | Frigg et al. | |
| 6,228,085 B1 | 5/2001 | Theken et al. | |
| 6,270,499 B1 * | 8/2001 | Leu et al. | 606/64 |
| 6,306,136 B1 | 10/2001 | Baccelli | |
| 6,322,562 B1 | 11/2001 | Wolter | |
| 6,348,052 B1 | 2/2002 | Sammarco | |
| 6,364,882 B1 | 4/2002 | Orbay | |
| 6,416,528 B1 * | 7/2002 | Michelson | 606/185 |
| 6,423,064 B1 | 7/2002 | Kluger | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,471,706 B1 * | 10/2002 | Schumacher et al. | 606/70 |
| D469,533 S * | 1/2003 | Bryant et al. | D24/155 |
| 6,503,281 B1 * | 1/2003 | Mallory | 623/22.15 |
| 6,506,191 B1 * | 1/2003 | Joos | 606/86 B |
| 6,527,776 B1 | 3/2003 | Michelson | |
| 6,533,789 B1 | 3/2003 | Hall, IV et al. | |
| 6,565,569 B1 | 5/2003 | Assaker et al. | |
| 6,575,975 B2 | 6/2003 | Brace et al. | |
| D479,331 S | 9/2003 | Pike et al. | |
| 6,623,486 B1 | 9/2003 | Weaver et al. | |
| 6,669,701 B2 | 12/2003 | Steiner et al. | |
| 6,719,759 B2 | 4/2004 | Wagner et al. | |
| 6,960,211 B1 * | 11/2005 | Pfefferle et al. | 606/282 |
| 7,044,953 B2 | 5/2006 | Capanni | |
| 7,128,744 B2 | 10/2006 | Weaver et al. | |
| 7,229,444 B2 * | 6/2007 | Boyd | 606/300 |
| 2002/0128654 A1 * | 9/2002 | Steger et al. | 606/69 |
| 2002/0147453 A1 * | 10/2002 | Gambale | 606/71 |
| 2003/0055429 A1 * | 3/2003 | Ip et al. | 606/69 |
| 2003/0163132 A1 * | 8/2003 | Chin | 606/61 |
| 2004/0073218 A1 | 4/2004 | Dahners | |
| 2004/0097936 A1 * | 5/2004 | Ebid | 606/69 |
| 2004/0210220 A1 * | 10/2004 | Tornier | 606/69 |
| 2005/0165400 A1 | 7/2005 | Fernandez | |
| 2006/0235400 A1 | 10/2006 | Schneider | |
| 2007/0016205 A1 | 1/2007 | Beutter et al. | |

FOREIGN PATENT DOCUMENTS

| | | |
|---|---|---|
| CH | 611147 A5 | 5/1979 |
| DE | 34 42 004 C1 | 4/1986 |
| DE | 43 41 980 A1 | 6/1995 |
| DE | 43 43 117 A1 | 6/1995 |
| DE | 44 38 264 A1 | 3/1996 |
| DE | 93 21 544 U1 | 10/1999 |
| DE | 198 32 513 A1 | 2/2000 |
| DE | 203 09 361 U1 | 9/2003 |
| EP | 0 053 999 A1 | 6/1982 |
| EP | 0 207 884 A2 | 1/1987 |
| EP | 0 410 309 A1 | 1/1991 |
| EP | 0 515 828 A1 | 12/1992 |
| EP | 0 530 585 A2 | 3/1993 |
| EP | 1 468 655 A2 | 10/2004 |
| FR | 742 618 | 3/1933 |
| FR | 2 233 973 A1 | 2/1975 |
| FR | 2 405 062 A1 | 6/1979 |
| FR | 2 405 705 A1 | 6/1979 |
| FR | 2 405 706 A1 | 6/1979 |
| FR | 2 496 429 A3 | 6/1982 |
| FR | 2 674 118 A1 | 9/1992 |
| FR | 2 827 500 * | 1/2003 |
| JP | 11299804 | 11/1992 |
| SU | 1 037 911 A | 8/1983 |
| SU | 1 279 626 A1 | 12/1986 |
| WO | WO 87/00419 | 1/1987 |
| WO | WO 88/03781 A1 | 6/1988 |
| WO | WO 96/29948 A1 | 10/1996 |
| WO | WO 97/09000 A1 | 3/1997 |
| WO | WO 00/53110 A1 | 9/2000 |
| WO | WO 00/66012 A1 | 11/2000 |
| WO | WO 01/54601 A1 | 8/2001 |
| WO | WO 02/096309 A1 | 12/2002 |
| WO | WO 03/007832 * | 1/2003 |
| WO | WO 03/007832 A1 * | 1/2003 |
| WO | WO 2004/089233 A1 | 10/2004 |

OTHER PUBLICATIONS

ACE Symmetry™ Titanium Upper Extremity Plates, ACE Medical Company.
International Search Report for International Application No. PCT/CH03/00604, mailed May 3, 2004, German language version.
International Search Report for International Application No. PCT/CH03/00604, mailed May 3, 2004, English language translation of the German language version.
International Preliminary Examination Report for International Application No. PCT/CH03/00604, mailed Jun. 20, 2005, German language version.
International Preliminary Examination Report for International Application No. PCT/CH03/00604, mailed Jun. 20, 2005, English translation of the German language version.

* cited by examiner

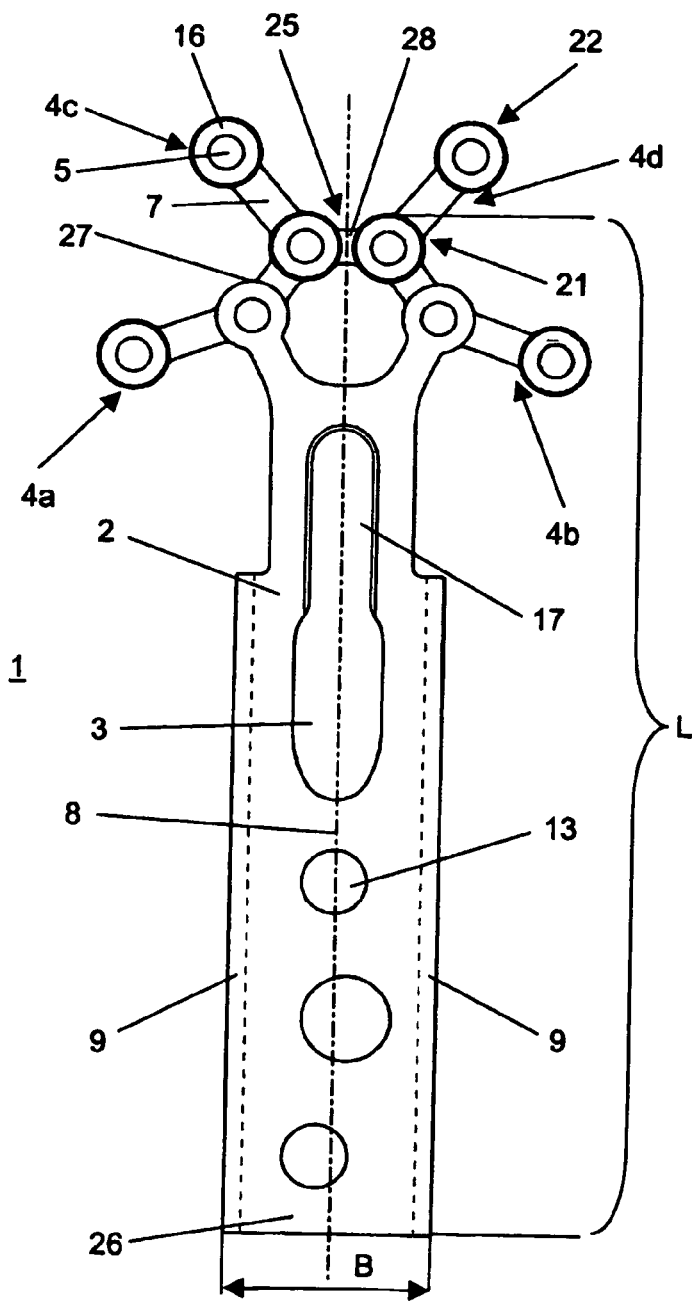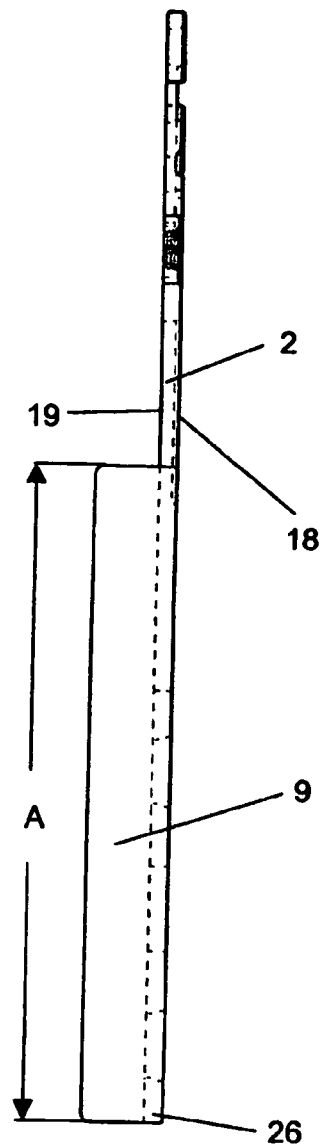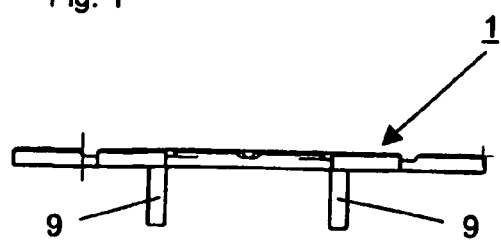
Fig. 1
Fig. 2
Fig. 3

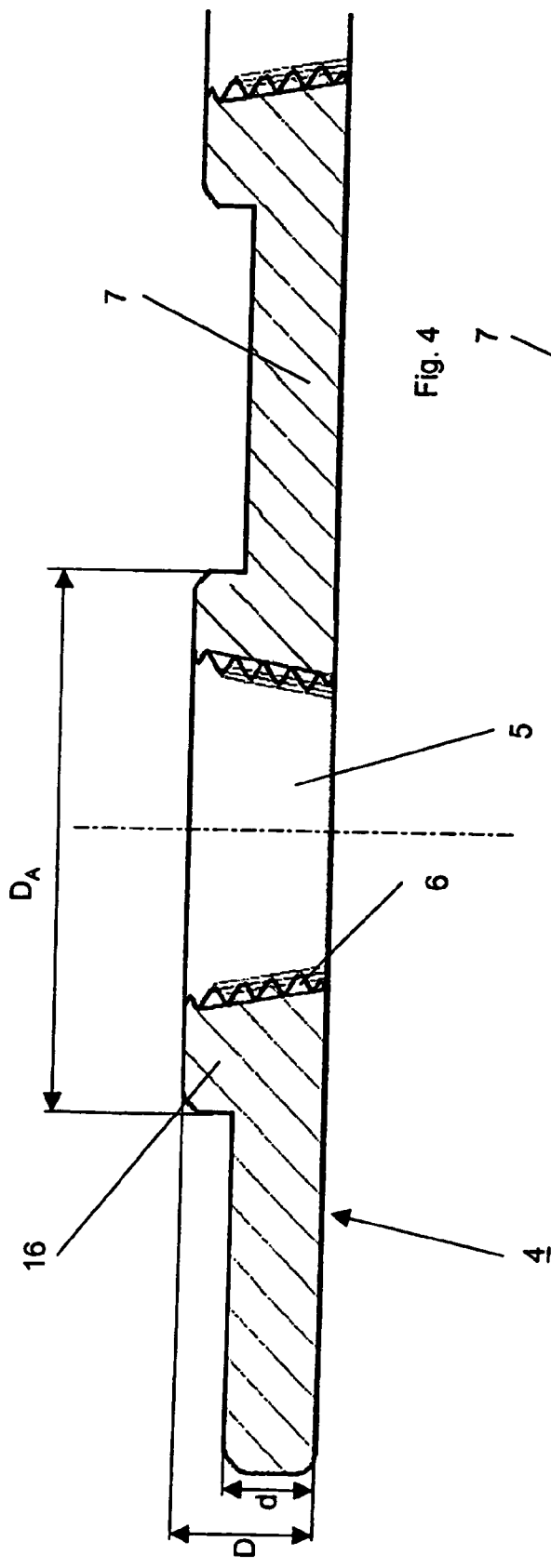
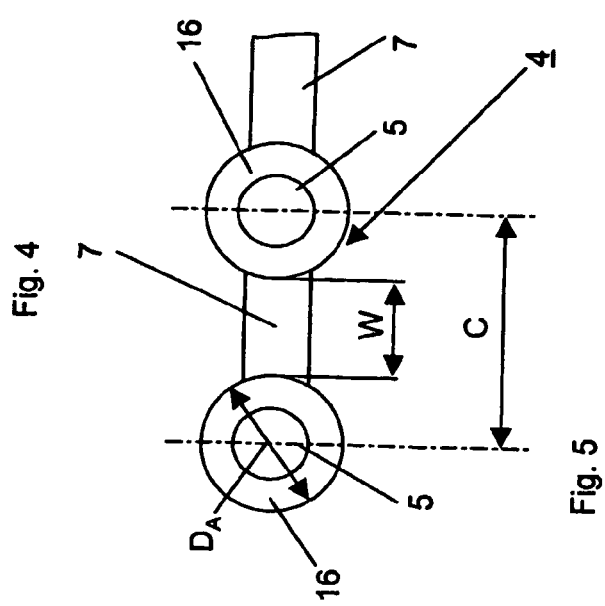

BONE-FIXATION DEVICE

RELATED APPLICATION DATA

The present application is a continuation of the U.S. National Stage designation of co-pending International Patent Application No. PCT/CH2003/000604, filed Sep. 8, 2003, the entire content of which is expressly incorporated herein by reference thereto.

FIELD OF INVENTION

The invention relates to a trochanter stabilization device for fixing bone fragments in the region of the hip joint, and to a hip screw device used with said trochanter stabilization device.

BACKGROUND OF INVENTION

Such devices are used for taking care of fractures at the proximal femur, especially unstable trochanteric fractures of the AO classification type 31-A2 and 31-A3.

Such a device is disclosed in EP 0 515 828 A1 and comprises a tubular link plate and a trochanter stabilization plate, which is detachably connected therewith. It is a disadvantage of this known device that:
the trochanter stabilization plate is relatively rigid and can hardly adapt itself to the respective anatomy;
angularly stable screws cannot be used;
the use of corticalis screws also is hardly possible, since the cortex is very thin in the region of the large trochanter and hardly permits any anchoring of the corticalis screws;
the fixation with cerclage is inadequate under some circumstances. In the case of this known plate, the large trochanter can be fixed only with the help of a cerclage wire. Under some circumstances, however, this type of fixation is insufficient for preventing dislocation in the cranial direction of the large trochanter, since the gluteus medius muscle, which engages the large trochanter, pulls with a force, which corresponds approximately to the weight of the body; and
the modularity is limited. With the known trochanter stabilization plate, it is not always possible to take into account the different anatomies and fracture configurations.

The German utility patent U1 87 06 912.1 discloses a small-bone plate for taking care of fractures of the skull skeleton and of the facial skeleton, that is, for an application other than for the fixation of bone fragments in a region in the vicinity of a joint. This known bone plate is constructed linearly, L-shaped, or as a double T, depending on its application, and has actually no central plate and, instead, is constructed on the whole as a conventional bone plate. This known plate therefore cannot be used for the fixation of bone fragments in an area in the vicinity of a joint.

SUMMARY OF THE INVENTION

The invention is to provide a remedy here. It is an object of the invention to provide a trochanter stabilization device, which comprises bone stabilization means, which can be adapted to the surface of the large trochanter.

Pursuant to the invention, this objective is accomplished by a trochanter stabilization device comprising a central plate having a longitudinal axis, an upper surface, a lower surface, and at least one opening through the plate from the upper surface to the lower surface configured for receiving a bone fixation element; and at least three arms extending from a first end of the central plate, each arm having an upper surface, a lower surface and at least one hole through the arm from the upper surface to the lower surface configured for receiving a bone fixation element. At least a portion of the hole in at least one of the arms may include internal threads. The device may also include a femoral implant, such as a hip screw or spiral blade, for introduction into the femoral head, and a sideplate having an angled sleeve configured for receiving the femoral implant. The sideplate and the central plate may be configured and adapted for placement of the central plate on the sideplate and fixation of both the sideplate and central plate to the femur.

The advantages, which can be achieved with the invention, are to be seen essentially therein that, due to the inventive device:
medialization of the shaft of the femur can be prevented, since the bone stabilization means, constructed as a trochanter stabilization plate, act as a lateral support;
the arms of the trochanter stabilization plate permit the fragments of the large trochanter to be held together and to be fixed;
the threaded holes in the proximal part of the trochanter stabilization plate permit the fragments of the large trochanter to be fixed stably with angularly stable screws, that is, bone screws, the head of which is fixed by means of a thread to the trochanter stabilization plate and, therefore, cannot be twisted or shifted with respect to the plate. By these means, any dislocation of the severed large trochanter in the cranial direction can be avoided. Otherwise, the biomechanics of the proximal femur might be adversely affected appreciably;
the trochanter stabilization plate is of modular construction in that it can be molded easily to the respective anatomy and trimmed. The plate is trimmed without the formation of burrs, since these can be separated only around the plate holes; and
the dynamizing mechanism of the hip screw is not affected. Moreover, an additional screw to prevent any rotation of the head of the femur can be used. In contrast to the known trochanter plate, the anti-rotation screw can be disposed at any convenient place in the case of the present trochanter plate.

In a preferred embodiment, the central plate of the bone stabilization means has a length L and a width B<L, as well as a longitudinal axis, while the arms are bone plate-shaped and have a width b<B. The arms comprise at least one sleeve having a hole. In each case, crosspieces are disposed between two sleeves or between a sleeve and the central plate. The essential advantage of this configuration of the arms lies therein that, if suitable dimensions are selected, the crosspieces have a length, which makes it possible that a standard cutting instrument, for example, a cutting instrument (AO No. 329.142) from the set of the Kalkaneus plate, can be used to sever the crosspieces.

Preferably, the sleeves have an external diameter $D_A$ of between 6 and 10 mm, while the distance C between two holes is between 10 mm and 15 mm.

In a different embodiment, the angle between two adjacent arms is at least 30° and preferably at least 40°. With that, the advantage can be achieved that, on the one hand, the above-mentioned cutting tool can also be used and, on the other, the screws can be screwed into the large trochanter at largely regular intervals.

In a preferred embodiment, the arms enclose an angle α, which ranges from ±5° to ±115°, and preferably from ±10° to ±110°, with the longitudinal axis of the central plate. In another preferred embodiments, the arms enclose an angle α which ranges from ±5° to ±90°, and preferably ±10° to ±80°, with the longitudinal axis (8).

In another preferred embodiment, at least a portion of the holes in the arms is provided with an internal thread. The following advantages can be attained due to this configuration:

- angularly stable connection of the bone fixation means, which are provided with an external thread complementary to the internal thread, especially bone screws in the arms of the bone stabilization means;
- the corticalis in the region of the large trochanter is very thin. For this reason, normal corticalis screws without a threaded knob can hardly be introduced except in the case of very young patients. On the other hand, with angularly stable screws, relative movement between the fixed fragments can be prevented even in very soft bones without a hard corticalis;
- screws without a threaded knob usually are used bicortically. This means that they must engage the opposite corticalis. Angularly stable screws, on the other hand, can also be used monocortically, as is necessary in the region of the large trochanter;
- the angularly stable screws make it possible to keep the plate at a distance from the bone. By these means, the circulation of blood through the periosteum is affected less. This may contribute to a more rapid healing of the bone.

Preferably, the internal thread in the holes is constructed conically, because it is considerably more difficult to screw head-locking screws with a cylindrical thread at the correct angle into the plate.

In a further embodiment, the thickness "D" of the arms, measured perpendicularly to the central plate in the region of the holes, is greater than the thickness "d" of the crosspieces connecting the individual holes. With that, the advantages can be attained that:

- when there is deformation, especially a bending of the arms for adapting to the anatomical conditions, the internal threads in the sleeves are not deformed by this configuration, so that their function is not affected by the deformation of the arms;
- the arms can be severed precisely at the transition from the crosspieces to the sleeves, so that burrs are not formed on the plate surface by the severing;
- the arms can be severed better because of the lesser wall thickness.

In yet a further embodiment, the arms are connected by crosspieces transversely to the longitudinal axis of the central plate. As a result, the advantage can be achieved that the sleeves may be connected in such a manner with one another so that the bone fragments are held together. Any displacement of the fragments of the large trochanter in the cranial direction should be avoided. The gluteus medius muscle pulls the large trochanter in the cranial direction with a force, which corresponds approximately to the weight of the body.

The bone stabilization means may be configured in such a manner that the length of the arms is at least 6 mm and preferably at least 8 mm. Each arm has at least one hole. The distance between two holes of the same arm may be less than 6 mm and preferably is between 3.5 mm and 4.5 mm. Furthermore, the distance between the most peripheral hole and the longitudinal axis, as seen from the central plate, may be between 10 mm and 40 mm.

In a different embodiment, the bone stabilization means consists of stainless steel with an elongation at break of at least 40%. Preferably, the metal alloy consists of 17.0 to 19.0% of chromium, 13.0 to 15% of nickel and 2.7 to 3.0% of molybdenum. The bone stabilization means preferably is produced from a soft material, so that the arms do not break when they are bent against the bone surface.

In yet another embodiment, the central plate has guide rails at its longitudinal sides perpendicular to the plate. Preferably, the width of the bone plate corresponds to the distance between the guide rails, so that the bone stabilization means, together with the central plate, may be shifted, for example, on a bone plate parallel to the latter.

In a further embodiment, the bone stabilization means and the bone plate have fastening perforations, which are matched to one another and into which bone fixation means, especially bone screws, can be introduced so that the bone stabilization means and the bone plate can be connected jointly with the bone.

In a preferred embodiment of the inventive hip screw device, the latter comprises an embodiment of the above-described trochanter stabilization device and a fastening element, which is constructed as a hip screw or as a spiral blade, for introduction into the sleeve.

BRIEF DESCRIPTION OF THE DRAWINGS

An example of the invention, which, at the same time, explains the principle by which the invention functions, is described in greater detail in the following and shown in the drawings, in which:

FIG. 1 shows a plan view of the bone stabilization means of an embodiment of the inventive trochanter stabilization device;

FIG. 2 shows a side view of the bone stabilization means of FIG. 1;

FIG. 3 shows a front view of the bone stabilization means of FIG. 1;

FIG. 4 shows a cross-section through a section of an arm of the bone stabilization means of FIGS. 1 to 3;

FIG. 5 shows a plan view of one of the arms of the bone stabilization means of FIGS. 1 to 3.

DETAILED DESCRIPTION OF THE PREFERRED EMBODIMENTS

Figure 6:
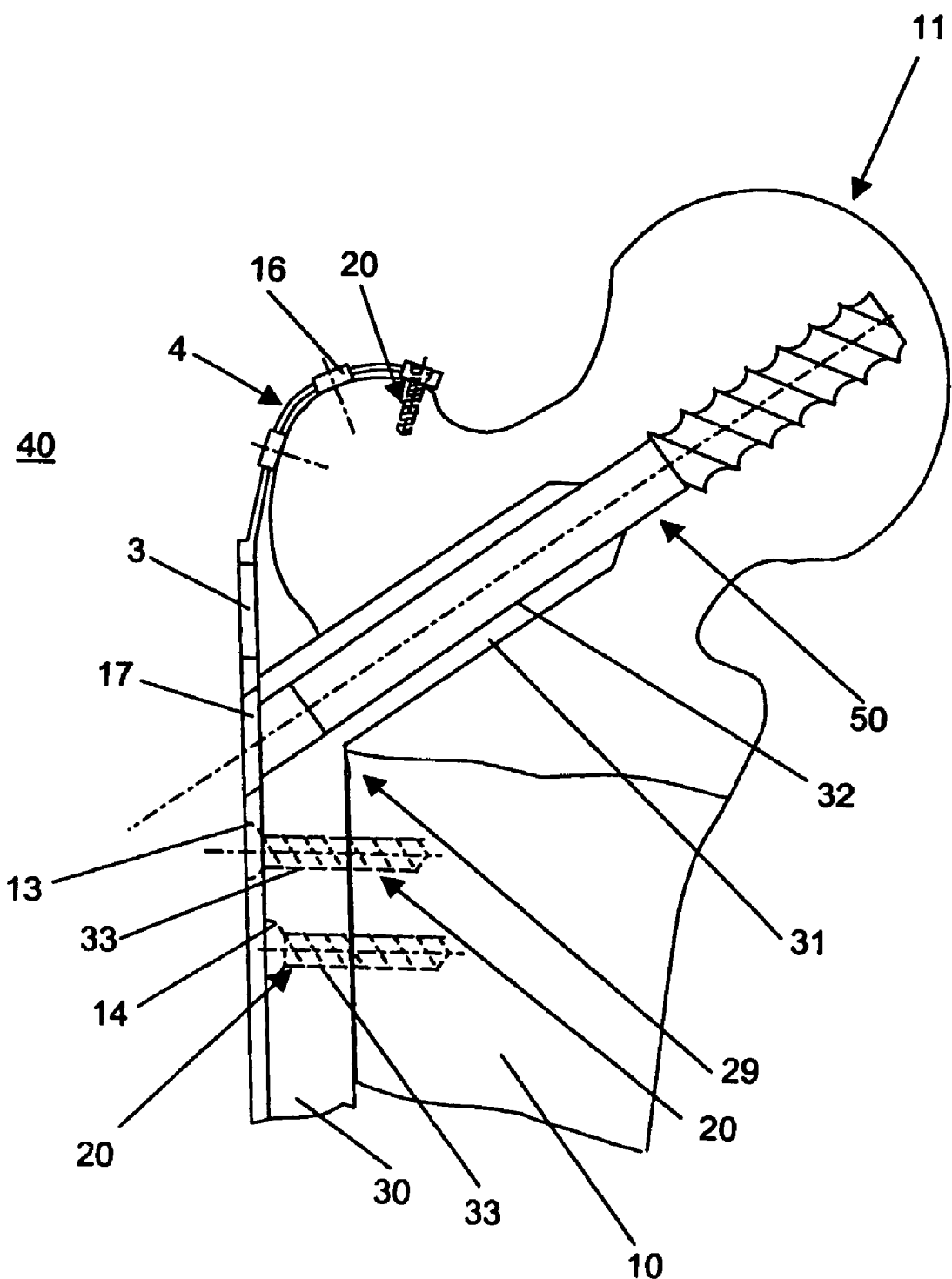
FIG. 6 shows a longitudinal section through a trochanter stabilization device with bone stabilization means of FIGS. 1 to 5 and a sleeve link plate, which comprises a bone plate and is mounted at the femur.

According to FIGS. 1 to 4, the bone stabilization means 1 comprises a central plate 2 with a longitudinal axis 8, an outer surface 18, which is averted from the bone 10, an inner surface 19 and four peripheral arms 4, which are angled or offset with respect to the longitudinal axis 8. Parallel to the longitudinal axis 8, the central plate 2 has a length L and, transversely thereto, a width B, B being smaller than L. Furthermore, the central plate 2 is provided with an elongated hole 3, which passes through the plate 2 from the outer surface 18 up to the inner surface 19, several fastening perforations 13, which also extend through the plate 2, and an opening 17, which likewise passes through the plate and terminates in the elongated hole 3. The arms 4 are disposed at the first end 25 of the plate 2, which intersects the longitudinal axis 8. Moreover, the plate 2 is forked at its first end 25 and provided at each of the fork tips 27 with a sleeve 16 having a hole 5 and comprises terminally an arc-shaped crosspiece 28, which connects the two fork tips 27 and two sleeves 16, each having a hole 5. The fixed ends 21 of two arms 4a, 4b are connected with the sleeves 16 at the fork tips 27, while the fixed ends 21 of the two other arms 4c, 4d are connected with the sleeves 16 at the crosspiece 28. Moreover, the arms 4a to 4d are disposed so that the two arms 4a, 4b, which are connected with the sleeves 16 at the fork tips 27, enclose an angle of approximately 110° with the longitudinal axis 8, while the two arms 4c, 4d, which are connected with the sleeves 16 at the crosspiece 28, enclose an angle of approximately 35° with the longitudinal axis 8.

The fastening perforations 13 are to accommodate bone fixation means 20, especially bone screws, by means of which the bone stabilization agent 1, together with the bone plate 30 of a sleeve link plate 29 (FIG. 6), can be fastened to the bone 10. The opening 17 is constructed as an elongated hole, so that, if necessary, an additional bone screw (not shown) can be introduced. Twisting of the head of the hip joint relative to the femur is prevented by this additional bone screw. The rear end of the fastening element 50 (FIG. 6), which may be constructed, for example, as a hip screw or as a spiral blade, can back out into the elongated hole 3 during axial displacements.

The arms 4 are composed here of a sleeve 16, which is disposed at the free end 22, and of a crosspiece 7, which is disposed between the sleeves 16 and the fixed end 21. The sleeves 16 have a thickness D and the crosspieces 7 have a lesser thickness d, so that the crosspieces 7 can be bent without deformation of the sleeves 16 and, in particular, of the internal thread 6 within the sleeves 16. The holes 5 in the sleeves 16 are constructed conically and provided with a conical internal thread 6.

Furthermore, two guide rails 9 are mounted at the central plate 2 parallel to the longitudinal axis 8 on a length A, measured from the second end 26 of the plate 2. By means of these guide rails 9, the central plate 2 can be shifted parallel to its longitudinal axis 8 on the bone plate 30 of the sleeve link plate 29 fastened at the bone 10 (FIG. 6), until the arms 4 contact the surface of the large trochanter 12 (FIG. 6).

A section of one of the arms 4 is shown in FIG. 5. So that a commercially available cutting instrument, such as the cutting instrument (AO No. 329.142) from the set of the Kalkaneus plate can be used, the following dimensions are selected for the sleeves 16 with the holes 5 and the crosspieces 7:

the distance C between two centers of two adjacent holes 5 is 14 mm;
the distance W between two adjacent sleeves 16 is 6 mm; and
the external diameter $D_A$ of the sleeves 16 is 8 mm.

The embodiment of the trochanter stabilizing device 40, shown in FIG. 6, consists essentially of a conventional sleeve link plate 29, as used for taking care of femoral neck fractures and, especially, of trochanteric fractures of the femur, as well as of the central plate 2, which is constructed as a trochanter stabilization plate with four peripheral arms (4), angled with respect to the longitudinal axis 8 of the central plate 2 (FIG. 1 to 4). The crosspieces 7 (FIG. 1) of the arms 4 can be bent so that the arms 4 lie in contact with the surface of the large trochanter 12. The sleeve link plate 29 comprises a bone plate 30, which can be connected with the bone 10, especially with the femur shaft, extending parallel to the longitudinal axis of the shaft of the femur and is provided with a number of fastening perforations 33, and a guide sleeve 31, which is disposed at an angle to the bone plate 30 and has a central borehole 32, through which a fastening element, 50, especially a hip screw or spiral blade, can be passed. Preferably, the fastening perforations 33 are disposed offset and are countersunk 14. Bone fixation means 20, configured as bone screws, may be used for fixing the bone plate 32 to the bone. So that the bone plate 30 may be adapted better anatomically to the curved bone surface, it is constructed as a hollow cylindrical sector, which is adapted to the bone surface.

The bone plate 30 and the central plate 2 can be shifted relative to one another and parallel to the longitudinal axis 8 by means of the guide rails 9, until the fastening perforations 13 in the central plate 2 are aligned with the fastening perforations 33 at the bone plate 30, so that the central plate 2 can be fastened to the sleeve link plate 29, by means of a part of the bone fixation means 20, especially the bone screws, which are to be screwed into the bone plate 30.

The conventional surgical technique for implanting the bone plate 30 consists therein that:

several boreholes of different diameter for introducing the fastening element 50 and the guiding sleeve 31, mounted at the sleeve link plate 29, into the center of the neck of the femur, are produced by means of one instrument in one step in the lateral-medial direction below the large trochanter;

subsequently, the fastening element 50 is brought into the neck of the femur, the correct depth for screwing it in being determined by means of a targeting device;

after that, the guiding sleeve 31 of the sleeve link plate 29 is pushed over the fastening element 50;

with the help of bone fixation means 20, constructed as bone screws, the sleeve link plate 29 is fixed to the shaft of the bone, the first and the third fastening perforations 33 of the sleeve link plate 29 being left empty;

the arms 4 of the trochanter plate are trimmed and bent to shape with the help of suitable instrumentation corresponding to the fracture configuration present;

subsequently, the central plate 2 is mounted over the fastening perforations 13, 33, passing through the central plate 2 and the bone plate 30, with the help of bone fixation agents 20 constructed as bone screws, and mounted at the already implanted sleeve link plate 29;

if required, a bone screw, with a diameter of at least 6.5 mm, may be brought through the opening 17 into the bone stabilization means 1 in order to prevent rotational movement between the head fragment and the femur shaft. At the same time, the bone stabilization means 1 may serve as a counter-hold, in order to pull the head fragment laterally and thus to close the fracture gap; and the bone fragments of the large trochanter can subsequently be fixed in position with the help of bone fixation means 20, especially with angularly stable bone screws with a threaded knob. Relative movement between the screws, and, accordingly, between the bone fragments is prevented by the angularly stable anchoring of the bone screws in the holes 5 of the bone stabilization means 1.

Because of its structural stiffness, the trochanter stabilization plate can be produced from a fairly thin sheet of metal.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. A device for repairing femoral fractures comprising,
a central plate extending along a longitudinal axis and having an upper surface, a lower surface and first and second sides connecting the upper surface to the lower surface, the central plate including at least one opening through the plate from the upper surface to the lower surface configured for receiving a bone fixation element, and a forked end including a first fork tip and a second fork tip that are connected to one another at distal ends via a crosspiece, each of the first fork tip and the second fork tip including a hole therethrough from the upper surface to the lower surface configured for receiving a bone fixation element;

at least one guide rail disposed along at least a portion of at least one of the first and second sides of the central plate, the at least one guide rail extending substantially perpendicular to the lower surface of the plate; and at least three arms extending from one of the crosspiece, the first fork tip and the second fork tip, a first one of the arms extending from the crosspiece, each arm having an upper surface, a lower surface and at least one hole through the arm from the upper surface to the lower surface configured for receiving a bone fixation element;

wherein at least a portion of the at least one hole in at least one of the arms includes internal threads.

2. The device of claim 1, wherein the first and second sides are substantially parallel to the longitudinal axis of the plate.

3. The device of claim 1, further comprising at least two guide rails disposed along the first and second sides of the central plate, the at least two guide rails extending substantially perpendicular to the lower surface of the central plate.

4. The device of claim 1, wherein the central plate has a length L along the longitudinal axis of the plate, and a width B substantially perpendicular to the longitudinal axis of the plate, where B<L.

5. The device of claim 4, wherein each of the at least three arms has a width b, where b<B.

6. The device of claim 1, wherein each of the at least three arms includes at least one sleeve around the at least one hole through the arm.

7. The device of claim 6, wherein each of the arms includes at least two sleeves, and each sleeve includes a hole through the arm from the upper surface to the lower surface.

8. The device of claim 7, wherein each of the two holes through each arm has a central axis, and a distance C between the central axes of the two holes in each arm is between 10 mm and about 15 mm.

9. The device of claim 7, wherein the distance between two holes of the same arm is less than 6 mm.

10. The device of claim 6, wherein the at least one sleeve has an external diameter $D_A$ of between 6 mm and about 10 mm.

11. The device of claim 6, wherein the arms have a thickness D at the sleeve, and a thickness d in portions adjacent the sleeve, where D>d.

12. The device of claim 1, wherein at least two adjacent arms form an angle of at least 30° with one another.

13. The device of claim 1, wherein the arms enclose an angle α, which ranges from ±5° to ±115° with respect to the longitudinal axis of the central plate.

14. The device of claim 13, wherein the angle α ranges from ±10° to ±80°.

15. The device of claim 1, wherein the internal threads are conical.

16. The device of claim 1, wherein the arms have a length of at least 6 mm.

17. The device of claim 1, wherein the maximum distance between a hole in an arm and the longitudinal axis of the central plate is between 10 mm and about 40 mm.

18. The device of claim 1, further comprising a bone fastener element having a threaded head configured to mate with the internal threads of the hole in at least one of the arms.

19. The device of claim 1, further comprising at least a fourth arm extending from one of the crosspiece, the first fork tip and the second fork tip.

20. A device for treating femoral fractures, comprising:

a central plate having a longitudinal axis, an upper surface, a lower surface, at least one opening through the plate from the upper surface to the lower surface configured for receiving a bone fixation element, and a forked end including a first fork tip and a second fork tip that are connected to one another via a crosspiece, each of the first fork tip and the second fork tip including a hole therethrough from the upper surface to the lower surface configured for receiving a bone fixation element, the central plate further including first and second sides substantially parallel to the longitudinal axis of the plate;

at least three arms extending from one of the crosspiece, the first fork tip and the second fork tip, a first one of the arms extending from the crosspiece, each arm having an upper surface, a lower surface and at least one hole through the arm from the upper surface to the lower surface configured for receiving a bone fixation element, at least a portion of the at least one hole in at least one of the arms including internal threads;

at least two guide rails disposed along the first and second sides of the central plate, the at least two guide rails substantially perpendicular to the lower surface of the central plate;

a femoral implant for introduction into the femoral head; and a sideplate having an angled sleeve configured for receiving the femoral implant wherein the sideplate and the central plate are configured and adapted for placement of the central plate on the side plate and fixation of both the sideplate and central plate to a femur.

21. The device of claim 20, wherein the sideplate includes at least one fastening hole that aligns with the at least one opening in the central plate such that both the sideplate and central plate can be jointly fastened to a bone using at least one bone fixation element.

22. The device of claim 20, wherein the femoral implant is a screw or a spiral blade.

23. A device for repairing femoral fractures comprising, a femoral head implant;

a sideplate having an angled sleeve configured for receiving the femoral implant, and at least one hole for receiving a bone fastener;

a central plate having a longitudinal axis, an upper surface, a lower surface, at least one opening through the plate from the upper surface to the lower surface configured for receiving a bone fastener, and a forked end including a first fork tip and a second fork tip that are connected to one another via a crosspiece, each of the first fork tip and the second fork tip including a hole therethrough from the upper surface to the lower surface configured for receiving a bone fixation element;

at least three arms extending from one of the crosspiece, the first fork tip and the second fork tip, a first one of the arms extending from the crosspiece, each arm having an upper surface, a lower surface and at least one threaded hole through the arm from the upper surface to the lower surface configured for receiving a bone fastener;

wherein the sideplate and the central plate are configured and adapted for attachment to a femur, and the at least three arms are configured for stabilizing trochanteric fractures of the femur.

24. The device of claim 23, wherein the sideplate includes at least one fastening hole that aligns with the at least one opening in the central plate such that both the sideplate and central plate can be jointly fastened to a bone using at least one bone fastener.

* * * * *